US006956929B2

(12) United States Patent
Wolf et al.

(10) Patent No.: US 6,956,929 B2
(45) Date of Patent: Oct. 18, 2005

(54) METHOD FOR CONTROLLING MODULATION OF X-RAY TUBE CURRENT USING A SINGLE TOPOGRAM

(75) Inventors: Heiko Wolf, Erlangen (DE); Christoph Süb, Erlangen (DE); Stefan Popescu, Erlangen (DE)

(73) Assignee: Siemens Aktiengesellschaft (DE)

( * ) Notice: Subject to any disclaimer, the term of this patent is extended or adjusted under 35 U.S.C. 154(b) by 84 days.

(21) Appl. No.: 10/660,146

(22) Filed: Sep. 11, 2003

(65) Prior Publication Data

US 2005/0058249 A1 Mar. 17, 2005

(51) Int. Cl.[7] .................................................. H05G 1/34
(52) U.S. Cl. ....................................... 378/109; 378/110
(58) Field of Search ............................... 378/8, 16, 95, 378/109, 110, 117

(56) References Cited

U.S. PATENT DOCUMENTS 5,379,333 A 1/1995 Toth ............................ 378/16
5,400,378 A 3/1995 Toth ............................ 378/16
5,696,807 A 12/1997 Hsieh ......................... 378/109
5,822,393 A * 10/1998 Popescu ..................... 378/108
6,094,468 A 7/2000 Wilting et al. ................. 378/8

* cited by examiner

*Primary Examiner*—Edward J. Glick
*Assistant Examiner*—Courtney Thomas
(74) *Attorney, Agent, or Firm*—Schiff Hardin LLP

(57) ABSTRACT

In a method for controlling the modulation of the tube current of an X-ray tube in the production of images using computed tomography, a single topogram of the examination subject is obtained and an orthogonal attenuation value is calculated therefrom, also making use of geometrical information associated with the position of the table on which the examination subject is disposed. In a subsequently-obtained computed tomography scan, the tube current is controlled using the orthogonal patient attenuation.

1 Claim, 4 Drawing Sheets

Patient examination
Begin
TOPO
Planning the SPI in the TOPO
Scan parameters
Scan
END Topogram evaluation
Read out TOPO raw data
Evaluate TOPO raw data
Read out max. attenuation from TOPO raw data
Determine patient extension via threshold values
mA and modulation per revolution

METHOD FOR CONTROLLING MODULATION OF X-RAY TUBE CURRENT USING A SINGLE TOPOGRAM

BACKGROUND OF THE INVENTION

1. Field of the Invention

The present invention is directed to a method for prescribing control parameters for modulating the tube current (mA modulation) of an X-ray tube in a computed tomography system.

2. Description of the Prior Art

In the production of images of an examination subject by means of computed tomography, it is known that by automatic matching of the tube current to the patient attenuation, a good image quality can be insured while simultaneously optimizing the X-ray dosage. In order to calculate the correct tube current, the patient attenuation must be known.

Conventionally, current matching has been undertaken either on the basis of the expertise of the CT operator, or by evaluation of two orthogonal overview exposures (topograms). Examples of such conventional control procedures are described in U.S. Pat. Nos. 5,400,378 and 5,379,33 and 5,696,507. The necessity of producing two topograms results in exposure of the patient to an additional radiation dose. It would be desirable, therefore, to be able to achieve sufficient precise modulation of the tube current using only a single topogram.

SUMMARY OF THE INVENTION

It is an object of the present invention to provide a method for controlling modulation of the tube current of an X-ray tube in a computed tomography system, wherein the control of the tube current modulation is accomplished on the basis of only a single topogram of the examination subject.

This object is achieved in accordance with the principles of the present invention in a method wherein only a single topogram of the examination subject is employed for controlling modulation of the tube current when a CT image of the examination subject is obtained, by additionally determining the geometrical extent of the patient. From this geometrical information, the patient attenuation can be determined to a good approximation using organ-specific linear coefficients of attenuation. This information is used to automatically adjust the tube current so as to control the modulation of the current during rotation of the gantry and advancement of the patient table. If an online automatic tube current system is available the method can be used to obtain preliminary information for the parameterization of the tube load computer.

In accordance with the invention, the topogram is evaluated immediately after the measurement at the host computer of the CT system. The maximum attenuation in the direction of projection is determined as a function of the table position, and is stored as a data vector. The orthogonal extension of the patient is calculated from the topogram using a threshold value. The orthogonal patient attenuation is calculated as the product of the orthogonal extension and the tabulated organ-specific linear attenuation coefficient.

In this manner, for each table position the attenuation is obtained in the lateral and a.p. directions. Before the beginning of the scan, it is thus possible with the inventive method to calculate the optimal tube current for a particular image quality, and the projection modulation amplitude for each table position. This allows a controlled automatic dosage procedure and, in the case of an online automatic dosage procedure, this calculation is used to initialize the tube load computer and for pre-setting the modulation software.

DESCRIPTION OF THE PREFERRED EMBODIMENTS

Figure 1:
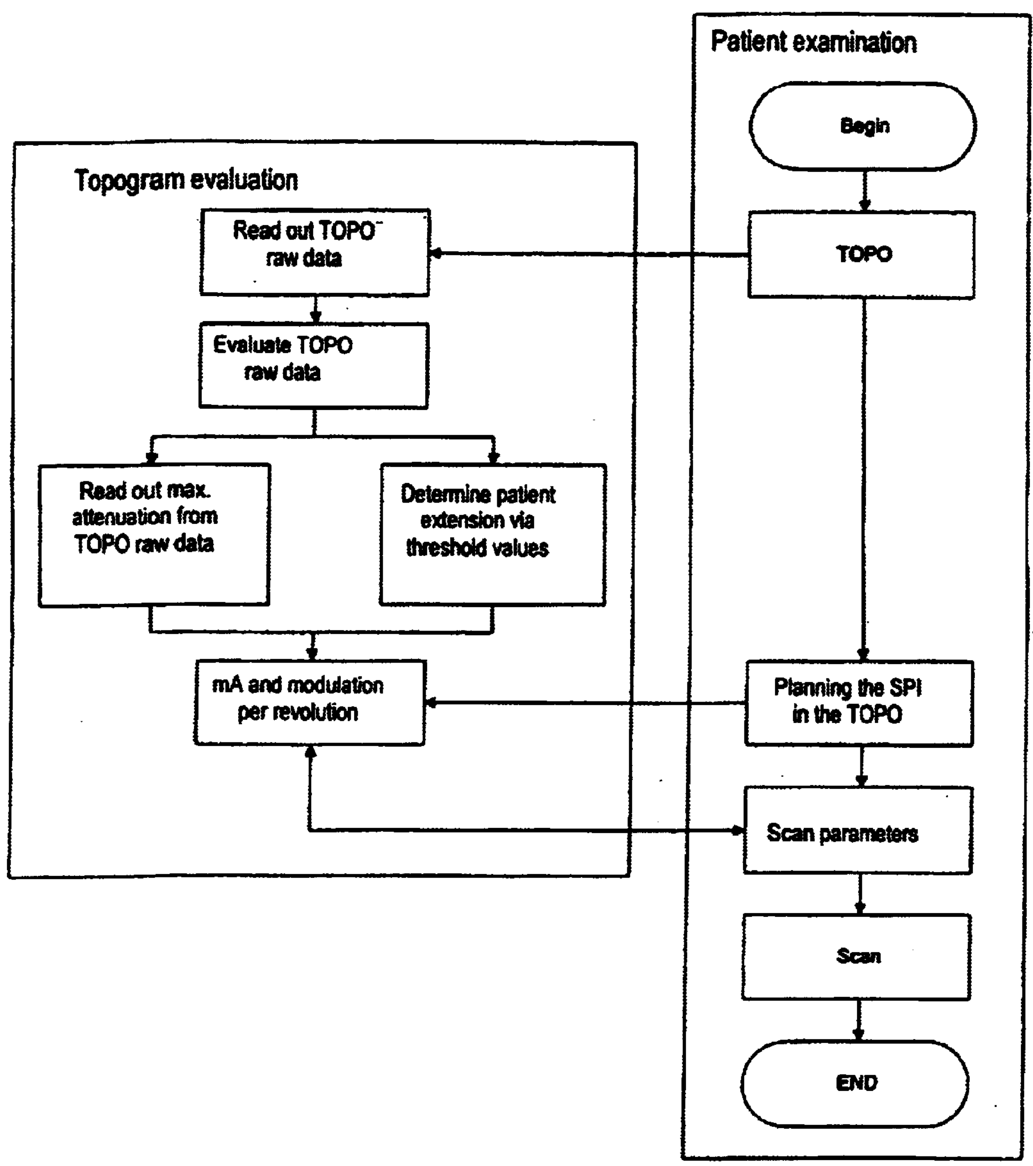
FIG. 1 is a flow chart for describing the steps of the inventive method.

The basic steps of the inventive method are schematically illustrated in FIG. 1. At the right of FIG. 1, the steps relating solely to the patient examination are shown, and at the left of FIG. 1 the steps relating to the evaluation of a single topogram are shown. The patient examination begins with the generation of a single topogram, and the single topogram is then read out and evaluated as raw data. The maximum attenuation is determined from the topogram raw data and the patient extension orthogonal to the projection direction is determined by evaluation of threshold values. The tube current (mA) and modulation per revolution are determined from the maximum attenuation and the patient extension, plus additional information relating to the patient examination, as needed. Scan parameters are then determined at least as a result of the topogram evaluation, but also possibly by manually entering other scan parameters. The scan is then conducted.

The following quantities can be directly determined from a single topogram:

for a.p. topogram maximum attenuation in a.p. direction (Sa.p.) and geometrical expanse in lateral direction (dlat)

for lateral topogram maximum attenuation in lateral direction (Slat.) and geometrical expanse in a.p. direction (da.p.)

The maximum attenuation was previously determined from the absolute maximum of the attenuation of a projection. The procedure causes unusable results given subjects with highly attenuating details (metals).

In order to be able to blank out such strong local attenuations, for example due to metallic implants, nails, screws and clips, a sliding averaging over a number of channels is implemented before the determination of the maximum attenuation in each projection. The use of 64 channels ($=2^6$) is suitable. This corresponds to a geometrical expanse of approximately 42 mm in the rotational center.

The expanse of the patient perpendicular to the transirradiation direction is estimated from the corresponding attenuation profile. A simple determination of the outside contour leads to results that are in part misleading, for example a.p. topograms in the thigh region. All channels whose attenuation value lies above a defined threshold therefore are determined. Air and bed regions as well as regions with very little attenuation are blanked out by means of this threshold.

The missing, second attenuation value, $S_{a.p.}$ (given an a.p. topogram) or, respectively, $S_{lat.}$ (given a lateral topogram) is calculated with the following equation via the subject expanse identified in this way and an assumed, average attenuation coefficient $\bar{\mu}$;

$$S_{a.p/lat.}=2294\cdot\bar{\mu}\cdot d_{a.p./lat.}$$

The minimum of the controlled tube current in % is calculated with the "root equation";

$$I_{\min} = \sqrt{\frac{S_{a.p.}}{S_{lat}}} \cdot 100\%$$

When the attenuation maximum is greater in the a.p. direction than in the lateral direction, then $l_{min}$>100% applies. This means that scanning is carried out with the maximum tube current at 90° and 270°.

Pronounced discontinuities in the boost between two table positions are adequately reduced or eliminated by weighted averaging over three or, respectively, five values.

Figure 2:
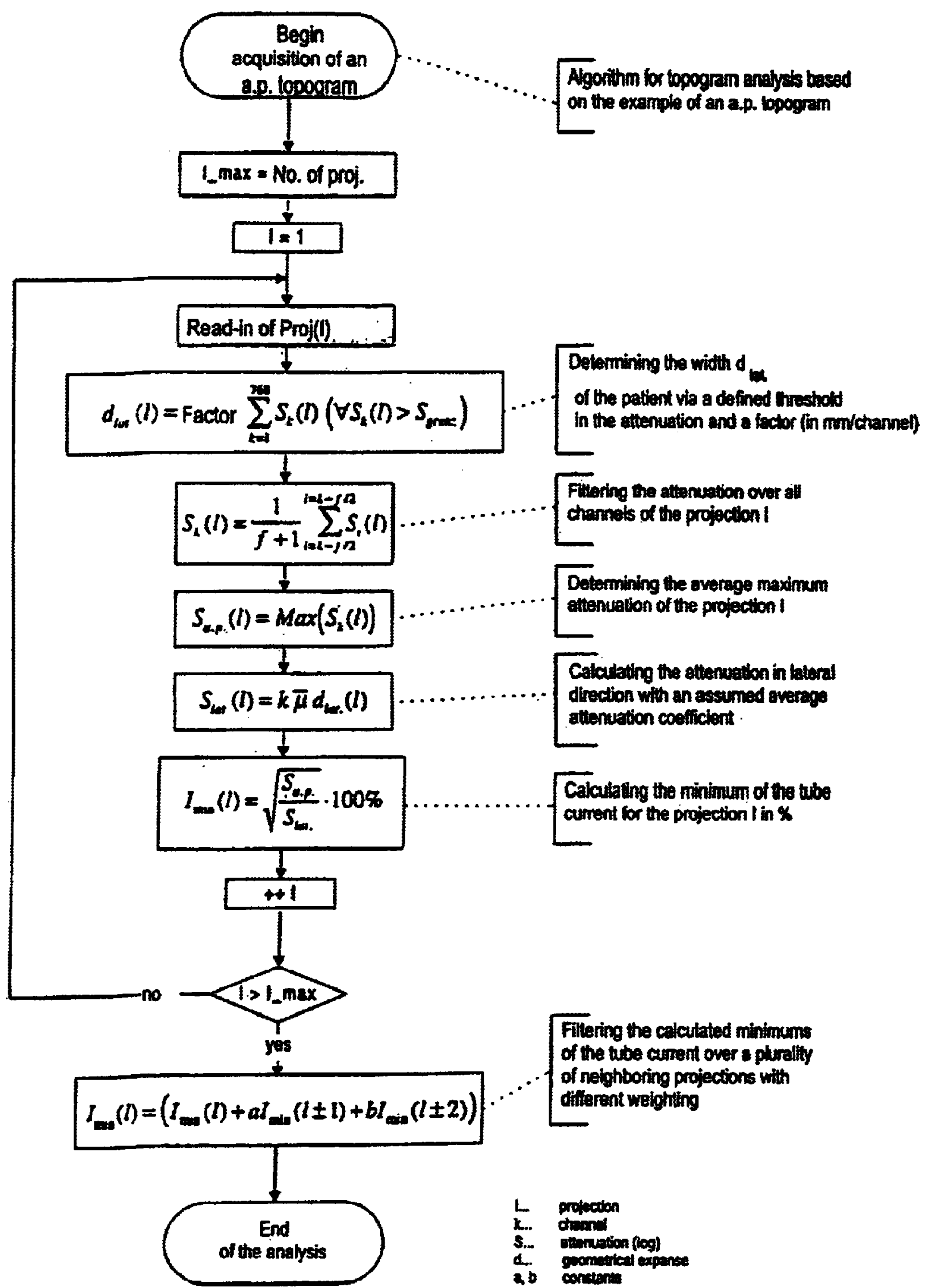
FIG. 2 is a detailed flow chart showing the mathematical algorithm for analyzing the topogram in accordance with the inventive method.

The flowchart shown in FIG. 2 provides an overview of the calculation of the control curve with the data from an a.p. topogram.

Ten topograms of patients (head, shoulder, lung, abdomen, pelvis) were evaluated with the method shown in FIG. 2. Insofar as possible, he results of the evaluation were compared to the actual attenuation values from spiral or sequence scans of the corresponding table positions.

The average attenuation coefficient $\bar{\mu}$ for calculating the attenuation S from the geometrical expanse is highly dependent on the organ examined. It fluctuates between approximately 0.15 $cm^{-1}$ for lung and 0.23 $cm^{-1}$ for slices with a relatively high proportion of bone (shoulder, head).

Figure 3:
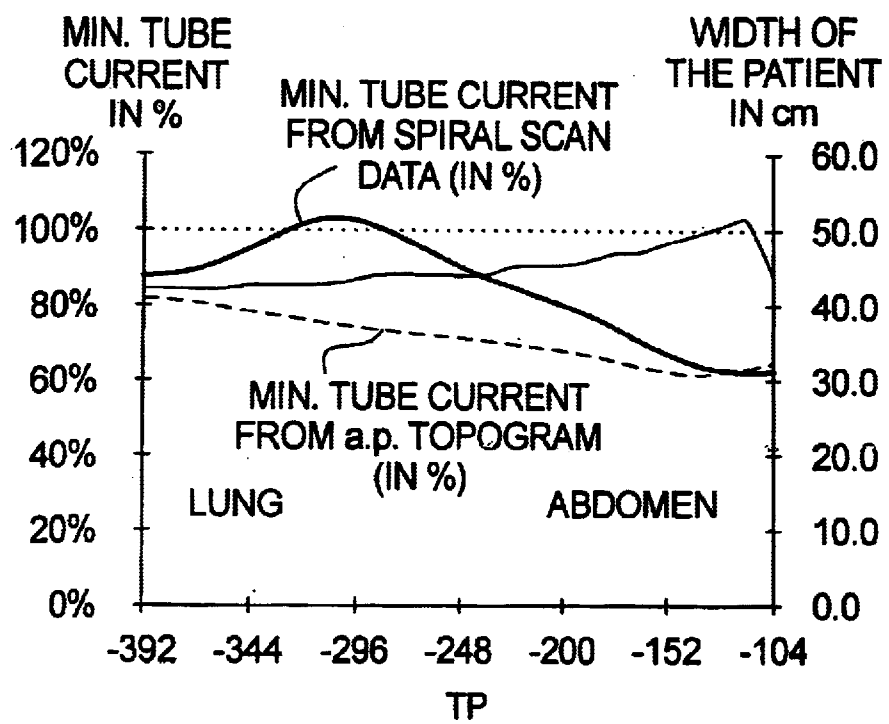
FIGS. 3 and 4 respectively illustrate control curves for controlling the tube current obtained by evaluating a single topogram, without the additional steps of the inventive method.

Despite an organ-specifically adapted average attenuation coefficient, the minimum tube current calculated from the topogram deviates on average by ±10–30% from the optimum parameters that were determined from spiral and sequence data (see FIG. 3).

It could be partly observed that the maximum of the tube current was shifted by 90°, which would lead to a deterioration of the image quality (see FIG. 3).

FIG. 3 shows, first, the control curve calculated from the a.p. topogram and, second the control curve that was acquired from the spiral data. When the two curves are compared, it is clear that the switch between the individual body sections (lung→abdomen) is not recognized given a nearly constant width of the patient. A deviation in the boost of >20% as well as an incorrect position of the maximum tube current are the consequences.

An a.p. and a lateral topogram were available for calculating this control curve/these control curves. In the determination of the control curve, the two topograms were separately analyzed with the algorithm described in Point 2. The control curve calculated with the attenuation maximums determined from both topograms served as comparison or, respectively, reference curve.

Figure 4:
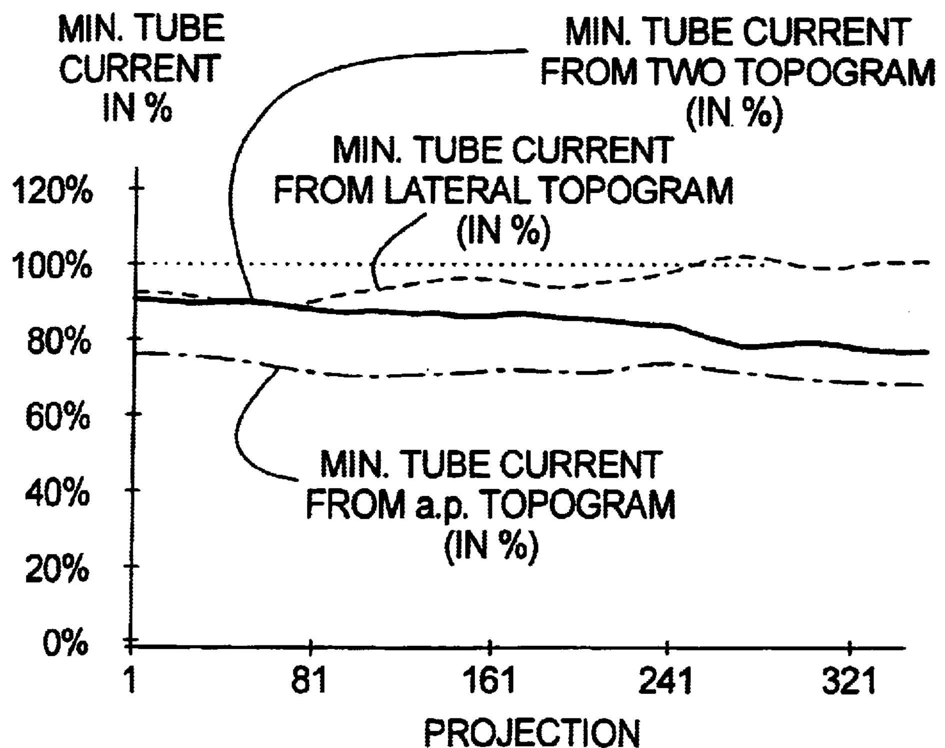

When the tendencies of the individual curves are viewed in FIG. 4, then the curve calculated from the a.p. topogram has a course similar to the reference curve, but with an average deviation of approximately 10–15%. The control curve that was calculated from the lateral topogram, in contrast, exhibits a totally different course. In part, the dose power maximum for this curve is also shifted by 90° (tube current >100%).

The information acquired from the topogram only serve as a default for the tube load computer and the first scan in a sequence or, respectively, the first revolution in the spiral. For all further scans or, respectively, revolutions, the a.p. and lat. attenuation values from the most recent 180° or 360° revolution are used for calculating the minimum tube current for the next revolution and, thus, the sinusoidal control curve is parameterized anew.

The following advantages are obtained:

By prescribing the minimum tube current for only the first scan (for example, as parameter in the mode table TF0), the transfer of the values for all other table positions can also be omitted. Thus, an addition of a further table for the attenuation conditions for each table position can be omitted in the host software or, respectively, firmware.

An attenuation coefficient is no longer required for the further determination.

Scanning for "additional scans" that lie outside the region that was covered by the topogram can also be done here with dose regulation.

Gantry tilting and the administration of contrast agent are recognized. An unusual patient geometry as well as patient positioning, however, can only be compensated by a true regulation.

Figure 5:
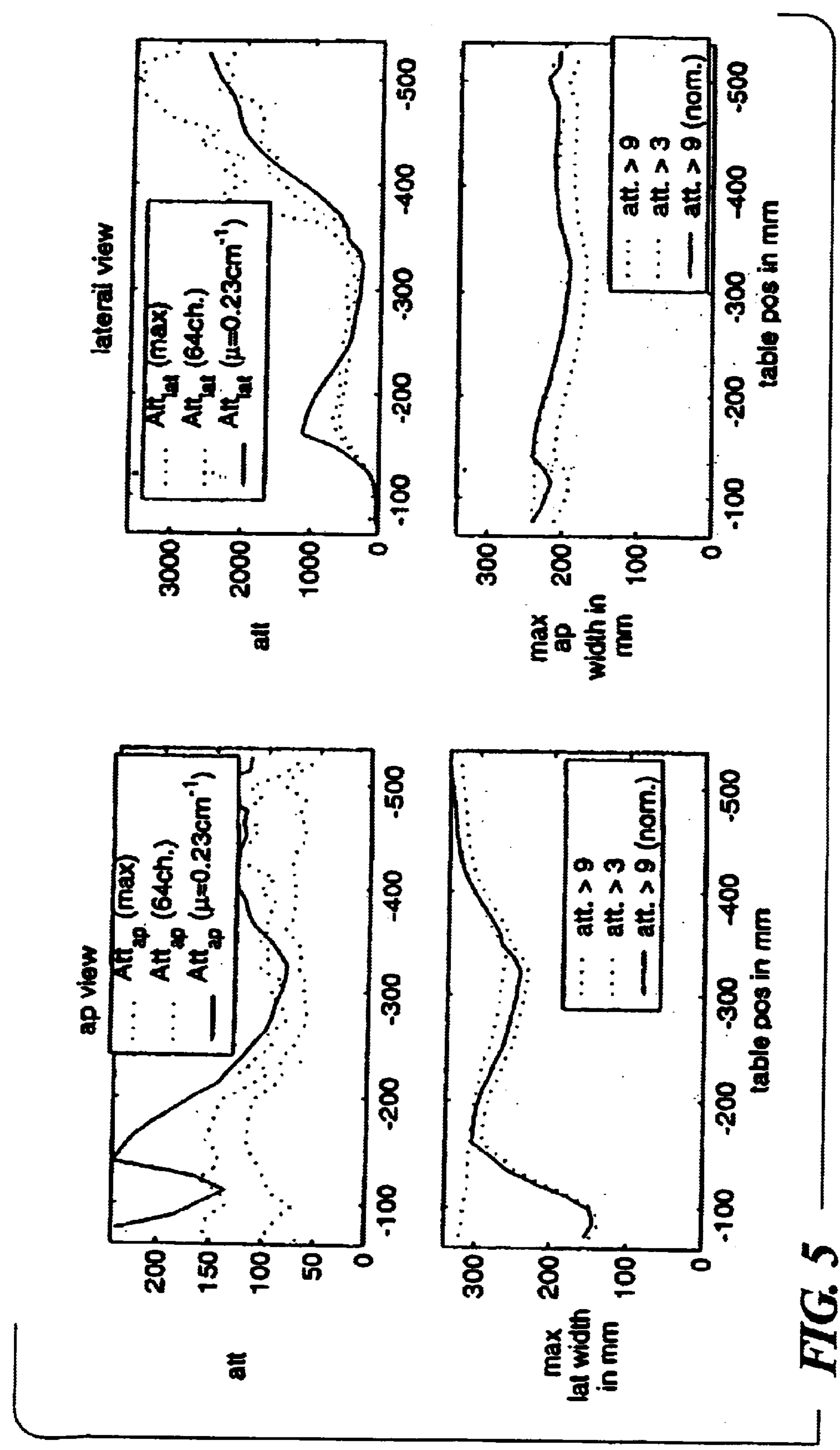
FIG. 5 shows examples of control curves obtained in accordance with the inventive method.

FIG. 5 shows examples of control curves that are obtained in accordance with the inventive method. As can be seen in comparison to the control curves shown in FIGS. 3 and 4, the precision of the control is significantly improved.

Although modifications and changes may be suggested by those skilled in the art, it is the intention of the inventors to embody within the patent warranted hereon all changes and modifications as reasonably and properly come within the scope of their contribution to the art.

What is claimed is:

1. A method for controlling the tube current in an X-ray tube for producing an image by computed tomography, comprising the steps of:

obtaining a single topogram of an examination subject on an examination table;

evaluating said topogram and determining therefrom a maximum attenuation in a projection direction of a CT image of the examination subject to be subsequently obtained, as a function of a position of the table; storing said maximum attenuation as a data vector;

determining an orthogonal extent of the examination subject from said topogram using a threshold value;

determining an orthogonal attenuation of the examination subject as a product of said orthogonal extent and a stored organ-specific linear attenuation coefficient; and subsequently obtaining a topogram by irradiating the examination subject with X-rays from an X-ray tube supplied with a tube current, and modulating said tube current dependent on said orthogonal attenuation.

* * * * *